US012766211B2

(12) United States Patent
Fensham et al.

(10) Patent No.: US 12,766,211 B2
(45) Date of Patent: Oct. 20, 2026

(54) INDICATOR, AND ASSOCIATED MANAGEMENT SYSTEMS AND METHODS USING THE SAME

(71) Applicant: NOEL CEDRIC FENSHAM, Durban (ZA)

(72) Inventors: Noel Cedric Fensham, Durban (ZA); Ian Howard Dunt, Cape Town (ZA)

(73) Assignee: NOEL CEDRIC FENSHAM, Durban (ZA)

(*) Notice: Subject to any disclaimer, the term of this patent is extended or adjusted under 35 U.S.C. 154(b) by 0 days.

(21) Appl. No.: 18/833,871

(22) PCT Filed: Jan. 26, 2023

(86) PCT No.: PCT/IB2023/050668
§ 371 (c)(1),
(2) Date: Jul. 26, 2024

(87) PCT Pub. No.: WO2023/144740
PCT Pub. Date: Aug. 3, 2023

(65) Prior Publication Data

US 2025/0177595 A1 Jun. 5, 2025

(30) Foreign Application Priority Data

Jan. 26, 2022 (ZA) ................................ 2022/01179

(51) Int. Cl.
*A61L 2/28* (2006.01)
*A61L 2/07* (2006.01)
(Continued)

(52) U.S. Cl.
CPC *A61L 2/28* (2013.01); *A61L 2/07* (2013.01); *G06K 7/1417* (2013.01); *G16H 40/20* (2018.01); *A61L 2103/15* (2026.01)

(58) Field of Classification Search
CPC .......... A61L 2/28; A61L 2/07; G06K 7/1413; G06K 7/1417
(Continued)

(56) References Cited

U.S. PATENT DOCUMENTS 6,485,978 B1 * 11/2002 Kirckof ................ G09F 3/0297 436/1
6,485,979 B1 * 11/2002 Kippenhan .............. A61L 2/28 436/1

(Continued)

FOREIGN PATENT DOCUMENTS

EP 2 347 772 A1 7/2011
JP 2010-220970 A 10/2010

OTHER PUBLICATIONS

International Search Report and Written Opinion dated May 25, 2023 from corresponding International Patent Application No. PCT/IB2023/050668, 19 pages.

*Primary Examiner* — Paultep Savusdiphol
(74) *Attorney, Agent, or Firm* — Ruggiero McAllister & McMahon LLC

(57) ABSTRACT

There are indicators, and associated management systems and methods using said indicators, particularly, though not necessarily exclusively, for use in medical sterilisation applications. The indicators have a planar strip-like body with indicator machine-readable information provided thereon. Advantageously, the indicator machine-readable information is obscured from being read by a suitable reader device until the indicator, or a portion thereof comprising the indicator machine-readable information, is exposed to pre-determined sterilisation condition/s thereby evidencing exposure to said sterilisation conditions.

8 Claims, 5 Drawing Sheets

(51) Int. Cl.
*G06K 7/14* (2006.01)
*G16H 40/20* (2018.01)
*A61L 103/15* (2026.01)

(58) Field of Classification Search
USPC ................................ 235/385, 492, 487, 494
See application file for complete search history.

(56) References Cited

U.S. PATENT DOCUMENTS

| | | | | |
|---|---|---|---|---|
| 6,488,890 | B1 * | 12/2002 | Kirckof | A61L 2/28 436/1 |
| 6,884,394 | B1 * | 4/2005 | Hehenberger | G01N 21/25 436/1 |
| 8,492,162 | B2 * | 7/2013 | Kippenhan | G16H 40/20 436/1 |
| 2003/0170901 | A1 * | 9/2003 | Kippenhan | A61L 2/24 435/31 |
| 2006/0240563 | A1 * | 10/2006 | Kippenhan | G16H 40/20 436/100 |
| 2007/0231191 | A1 * | 10/2007 | Jung | A61L 2/07 422/3 |
| 2010/0217620 | A1 * | 8/2010 | Kippenhan | A61L 2/24 705/2 |
| 2018/0071421 | A1 * | 3/2018 | Fang | A61L 2/16 |

* cited by examiner

INDICATOR, AND ASSOCIATED MANAGEMENT SYSTEMS AND METHODS USING THE SAME

CROSS-REFERENCE TO RELATED APPLICATIONS

The present application is a national phase application claiming priority from PCT Application No. PCT/IB2023/050668, filed Jan. 26, 2023, which claims priority from South Africa Patent Application No. 2022/01179, filed Jan. 26, 2022, the disclosure of which are incorporated herein in their entireties.

FIELD OF DISCLOSURE

This disclosure relates to indicators, and associated management systems and methods using said indicators, particularly, though not necessarily exclusively, for use in medical sterilisation applications.

BACKGROUND OF THE DISCLOSURE

In conventional circumstances, when a patient is admitted at a hospital or other healthcare facility for a theatre procedure requiring surgical incision and possibly further prosthetic material insertion, a supplier provides theatre or medical sets for the theatre procedure containing the necessary instruments and/or implants, not all of which will be utilised.

Post-procedure, the balance or remaining implants and/or the instruments in these theatre sets are washed and returned to the supplier which then washes, cleans, and re-constitutes (but does not sterilize) the medical sets for storage and/or dispatch to a hospital when required for a theatre procedure.

The medical facility, typically a hospital, is required to steam autoclave sterilize the sets prior to theatre use. Steam autoclaving is a sterilisation methodology which is conventionally used in healthcare settings such as hospitals and clinics to sterilize medical equipment for example, equipment such as unused implants, theatre/medical kits, and the like used in surgery.

It is of utmost importance that the protocol of autoclave efficacy is followed daily, with the inclusion of test packs or indicators indicating proper maintenance and effective sterilization.

Conventionally, chemical indicators used for detecting steam in the autoclave during sterilization are made into or incorporated within cards, bars, tapes and the like which are provided with the articles to be sterilised in the autoclave so as to confirm that the articles being sterilized have indeed been exposed to the required pressure and/or temperature required for sterilisation thereof.

Autoclave tape is commonly used to seal the articles such as theatre sets to be sterilized and to indicate whether the material package has been autoclaved, so as to avoid the confusion between autoclaved and un-autoclaved medical sets. Autoclave tape is normally made of a pressure and/or temperature sensitive adhesive tape comprising an indicator which is visually responsive to the pressure and/or temperature conditions in the autoclave so as to visually indicate that the set has been effectively sterilised by changing colour.

The Applicant has identified that it is not ideal to apply conventional autoclave tape to the outside of the theatre/medical set containers as these are made of metal which may affect the operation of the tape as the same should ideally not be in direct contact with metal. Moreover, the Applicant has recognised that there is a need to provide a system and methodology to manage the sterilisation of medical equipment such as theatre sets so as to limit the risk of contamination and to provide a auditable trail for the sterilisation of medical equipment.

SUMMARY OF THE DISCLOSURE

According to a first aspect of the disclosure, there is provided an indicator comprising a body and indicator machine-readable information provided on the body, wherein the indicator machine-readable information is obscured from being read by a suitable reader device until the indicator, or a portion thereof comprising the indicator machine-readable information, is exposed to predetermined sterilisation condition/s.

Differently stated, the indicator machine-readable information may change from an un-readable to a readable condition in response to exposure to the predetermined sterilisation condition/s, wherein in the un-readable condition, the indicator machine-readable information is not readable by the suitable reader device, and in the readable condition, the indicator machine-readable information is visible and/or visually presented and/or accessible and/or is revealed and/or is readable by the suitable reader device 22.

The predetermined sterilisation condition/s may be one, or more, of a predetermined temperature, moisture level or moisture in the form of steam for a predetermined amount of time, and pressure after which the indicator machine-readable information is revealed to be read by the suitable reader device. The predetermined sterilisation condition/s may be conditions present in an autoclave which sterilises articles.

It will be appreciated that the indicator machine-readable information may only be exposed or revealed for reading by the reader device in response to the indicator, or a portion thereof, being exposed to a predetermined temperature and/or pressure and/or moisture. In this way, the ability of the reader device to read the indicator machine-readable information may be indicative of the indicator, or part thereof, being exposed to a predetermined pressure and/or temperature and/or moisture.

The predetermined temperature may be approximately 134° C.

The predetermined moisture or moisture level may be as a result of saturated steam for a predetermined amount of time. The predetermined amount of time may be three minutes.

The predetermined temperature and/or pressure and/or moisture may be associated with a temperature and/or pressure and/or moisture at which sterilisation of articles occurs. For example, the temperature and/or pressure and/or moisture which articles in an autoclave is required to be exposed to in order to be sterilized. In this regard, the indicator may be an autoclave indicator configured to indicate whether or not article/s associated with the indicator The body may comprise article detail machine-readable information which may read by a suitable reader device to provide information indicative of a batch number and/or serial number associated with article/s associated with the indicator. The reader device which is configured to read the indicator machine-readable information may also be configured to read the article detail machine-readable information. In some example embodiments, the article detail machine-readable information comprises human readable information.

The machine-readable information described herein (i.e., the indicator machine-readable information or the article detail machine-readable information) may be a machine-readable code, for example, Quick Response Code (QR code), a bar code, or the like capable of being read by a suitable reader. The suitable reader may be an optical reader configured to optically read the machine-readable codes. It will be appreciated that the suitable reader devices may be configured to read the machine-readable information to determine data associated therewith, for example, a description of the product, a sterilisation confirmation code, or the like.

The body may be a strip-like body. The body may be segmented into a plurality of panels which may be folded on each other in a concertina fashion, in use. Each panel, apart from the end panels which have free ends, may be bounded by seams, wherein the body is folded on each other in a concertina fashion along the seams. Adjacent panels of the body may be adhered to each other via suitable adhesives. For example, peripheries of the panels may be removably attachable to each other via a suitable adhesive provided at peripheries of the panel. The indicator machine-readable code may be provided on one of the panels. In this way, the indicator with the indicator machine-readable information thereon is not contaminated or compromised, in use.

In some example embodiments, the indicator machine-readable information may be printed onto the body with an ink which is chemically responsive to the predetermined temperature and/or pressure and/or moisture to be visible for reading by the reader device. In other example embodiments, the indicator machine-readable information is printed onto the body and is obscured by an opaque chemical compound which becomes more transparent after exposure to the predetermined temperature and/or pressure and/or moisture thereby permitting the indicator machine-readable information to be read by the reader device. In other example embodiments, the indicator machine-readable information is printed onto the body and is obscured by a chemical compound which changes colour after exposure to the predetermined temperature and/or pressure and/or moisture thereby permitting the indicator machine-readable information to be read by the reader device. In any event, it will be noted that the indictor machine-readable information is only visible once the indicator has been exposed to the predetermined temperature and/or pressure and/or moisture.

In some example, embodiments, the body may comprise a substrate and an adhesive backed layer located on the substrate. The indicator machine-readable information may be provided on the adhesive backed layer.

The indicator machine-readable information may be printed on a substrate and may be the same colour as the substrate so that it is not visible or readable until it is exposed to one, or more, of a predetermined temperature, moisture, or pressure.

The indicator machine-readable information may be printed onto the substrate with a conventional ink used in sterilisation methodologies for use with autoclaves.

According to a second aspect of the disclosure, there is provided a method of managing sterilisation of articles, the method comprises:

- providing an indicator as described herein with an article or a set of articles to be sterilised by way of heat and/or pressure and/or moisture in the form of steam for a predetermined period of time, for example, in an autoclave;
- recording the article detail machine-readable information and storing the same, and/or data associated therewith, in a database;
- reading the indicator machine-readable information by way of a suitable scanner device and storing the same, and/or data associated therewith, in the database; and
- associating the read indicator machine-readable information, and/or data associated therewith, with the recorded article detail machine-readable information, and/or data associated therewith in the database, wherein a successful reading of the indicator machine-readable information is indicative of the article or set of articles being sterilized at the predetermined temperature and/or pressure and/or moisture.

The step of recording the article detail machine-readable information may comprise reading the same with a reader device.

Moreover, it will be understood that the step of recoding and the step of reading may be initiated after a sterilisation process has occurred.

The articles may be medical equipment to be sterilised. The set of articles may be a theatre set to be sterilised.

The machine-readable information may be removed from the substrate and adhered to patient charge sheets. The indicator machine-readable information may be associated with a patient in the database so as to track use of the article or set of articles with the patient. The method may therefore comprise a step of associating the indicator machine-readable information with the patient, particularly patient data associated with the patient, in the database. Details of the article or set of articles may also be associated with the patient. In this way, an auditable trail of usage or and/or sterilization of articles used or to be use on a patient is maintained in the database. It will be understood that in order to comply with various legislation such as Acts which protect personal information, for example, the Protection of Personal Information Act, 2013 in South Africa, any patient information of a personal nature may be encrypted in the database and/or from being read by any reader device. It follows that only authorised reader devices will be able to read the indicator machine-readable information to protect the information of the patient. Patient data for the purposes of the present disclosure may be selected from a group comprising a patient's name, contact detail/s, residential address/es, physician's details, hospital admission number, medical aid details, details pertaining to the medical procedure which the patient is to undergo or has undergone, and other similar information, which at least is usable to be able to identify the patient.

A successful reading of the indicator machine-readable information may be when, orin instances wherein, the reader device is capable of reading the same. As mentioned herein, this is because the indicator machine-readable information is obscured until the predetermined temperature and/or pressure and/or moisture has been reached or exceeded.

According to a third aspect of the disclosure, there is provided a system of managing sterilisation of articles, wherein the system comprises:

- a database storing data; and
- one or more processors communicatively coupled to the database and one or more suitable reader devices, wherein the one or more processors are configured to:
  - receive and store in the database, article detail machine-readable information, and/or data associated therewith, from an indicator as described herein, wherein the indicator is provided with an article or a set of articles to be sterilised by way of heat and/or pressure and/or moisture in the form of steam for a predetermined period of time, for example, in an autoclave;

receive and store in the database, indicator machine-readable information, and/or data associated therewith, read by way of a suitable scanner device;

associate the received indicator machine-readable information, and/or data associated therewith, with the received article detail machine-readable information, and/or data associated therewith, in the database, wherein a successful reading of the indicator machine-readable information is indicative of the article or set of articles being sterilized at the predetermined temperature and/or pressure and/or moisture.

The one or more recording the article detail machine-readable information may comprise reading the same with a reader device.

According to a fourth aspect of the disclosure, there is provided a method of managing exposure of one or more article/s to predetermined sterilisation condition/s, wherein the method comprises:

providing an indicator as described herein with the one or more article/s;

reading the indicator machine-readable information by way of a suitable scanner device and storing the same, and/or data associated therewith, in the database, wherein a successful reading of the indicator machine-readable information is indicative of the one or more article/s being exposed to the predetermined sterilisation conditions.

According to a third aspect of the disclosure, there is provided a system for managing exposure of one or more article/s to predetermined sterilisation condition/s, wherein the system comprises:

a database storing data; and one or more processors communicatively coupled to the database and one or more suitable reader devices, wherein the one or more processors are configured to:

receive, and store in the database, indicator machine-readable information, and/or data associated therewith, read by way of a suitable scanner device from an indicator as described herein, wherein the indicator is provided with the one or more article/s, wherein a successful reading of the indicator machine-readable information is indicative of the one or more article/s being exposed to predetermined sterilisation condition/s.

DETAILED DESCRIPTION OF THE DRAWINGS

The following description of the disclosure is provided as an enabling teaching of the disclosure. Those skilled in the relevant art will recognise that many changes can be made to the embodiment described, while still attaining the beneficial results of the present disclosure. It will also be apparent that some of the desired benefits of the present disclosure can be attained by selecting some of the features of the present disclosure without utilising other features. Accordingly, those skilled in the art will recognise that modifications and adaptations to the present disclosure are possible, and may even be desirable in certain circumstances, and are a part of the present disclosure. Thus, the following description is provided as illustrative of the principles of the present disclosure and not a limitation thereof.

It will be appreciated that the phrase "for example," "such as", and variants thereof describe non-limiting embodiments of the presently disclosed subject matter. Reference in the specification to "one example embodiment", "another example embodiment", "some example embodiment", or variants thereof means that a particular feature, structure or characteristic described in connection with the embodiment(s) is included in at least one embodiment of the presently disclosed subject matter. Thus, the use of the phrase "one example embodiment", "another example embodiment", "some example embodiment", or variants thereof does not necessarily refer to the same embodiment(s).

Unless otherwise stated, some features of the subject matter described herein, which are, described in the context of separate embodiments for purposes of clarity, may also be provided in combination in a single embodiment. Similarly, various features of the subject matter disclosed herein which are described in the context of a single embodiment may also be provided separately or in any suitable sub-combination.

The headings used herein are for organizational purposes only and are not meant to be used to limit the scope of the description or the claims. For brevity, the word "may" is used in a permissive sense (i.e., meaning "having the potential to"), rather than the mandatory sense (i.e., meaning "must").

The words "include," "including," and "includes" and the words "comprises", "comprising", and "comprises" mean including and comprising, but not limited to, respectively.

Figure 1:
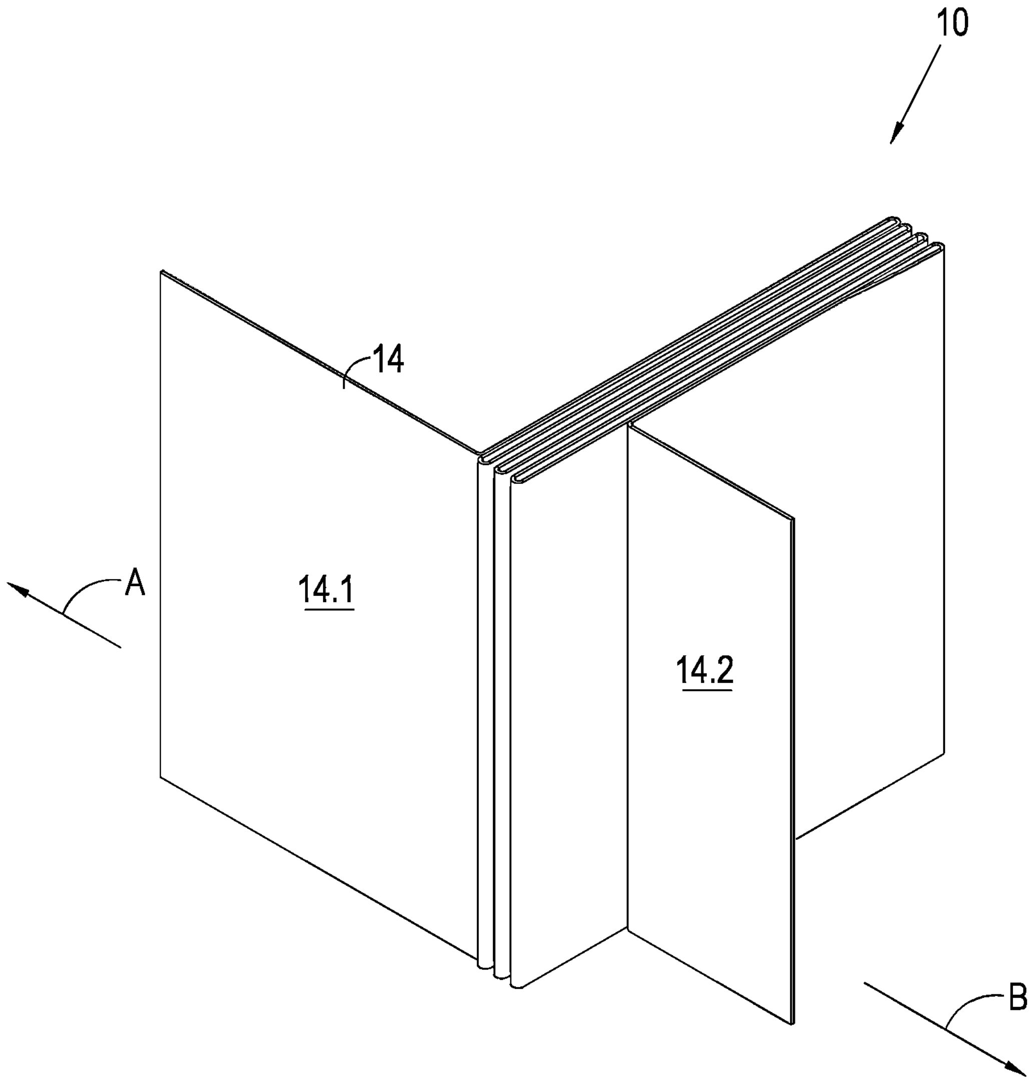
FIG. 1 shows a perspective view of an indicator in accordance with an example embodiment of the disclosure in a folded condition.
Figure 2:
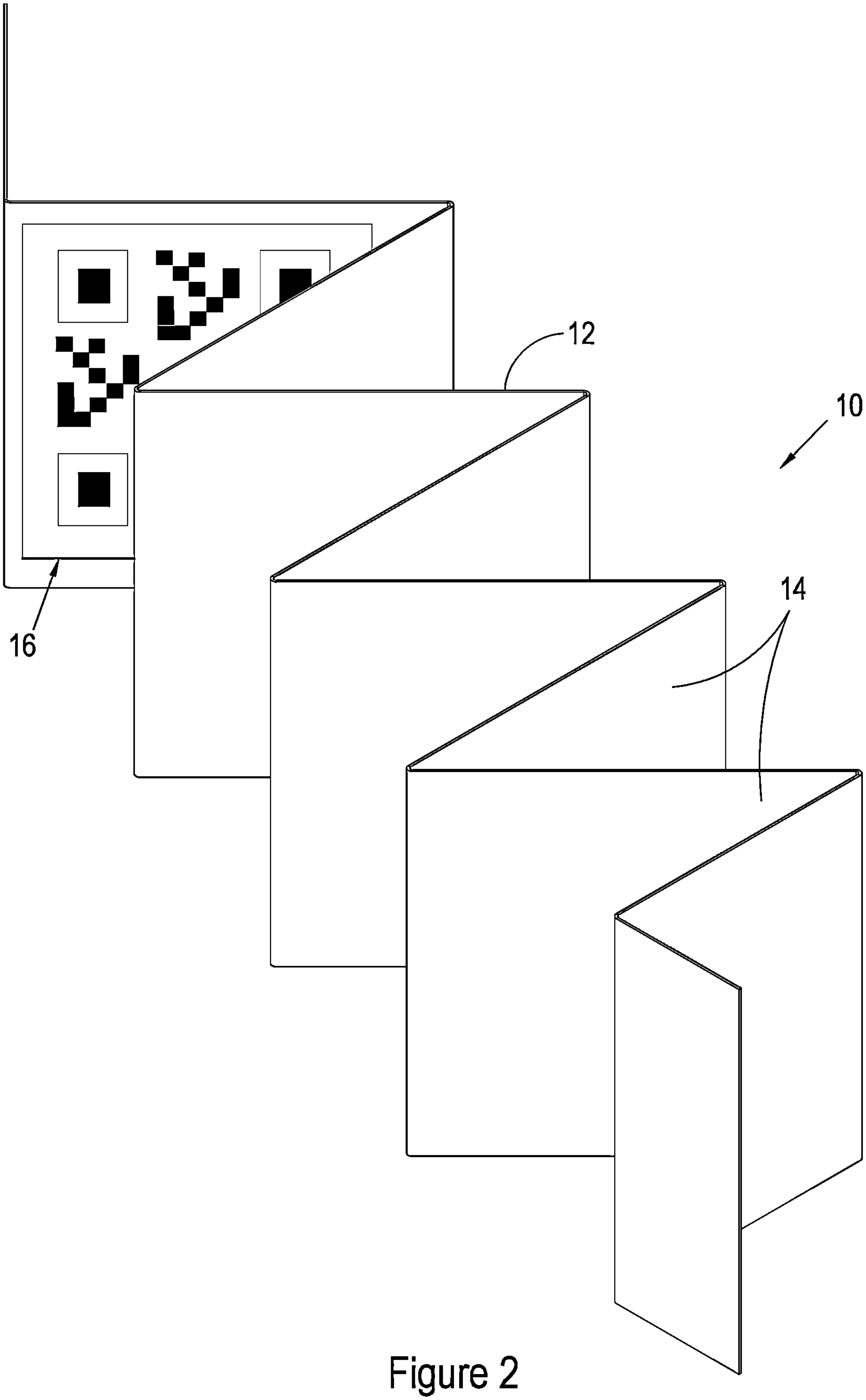
FIG. 2 shows another perspective view of an indicator in accordance with an example embodiment of the disclosure in a partially unfolded condition.
Figure 3:
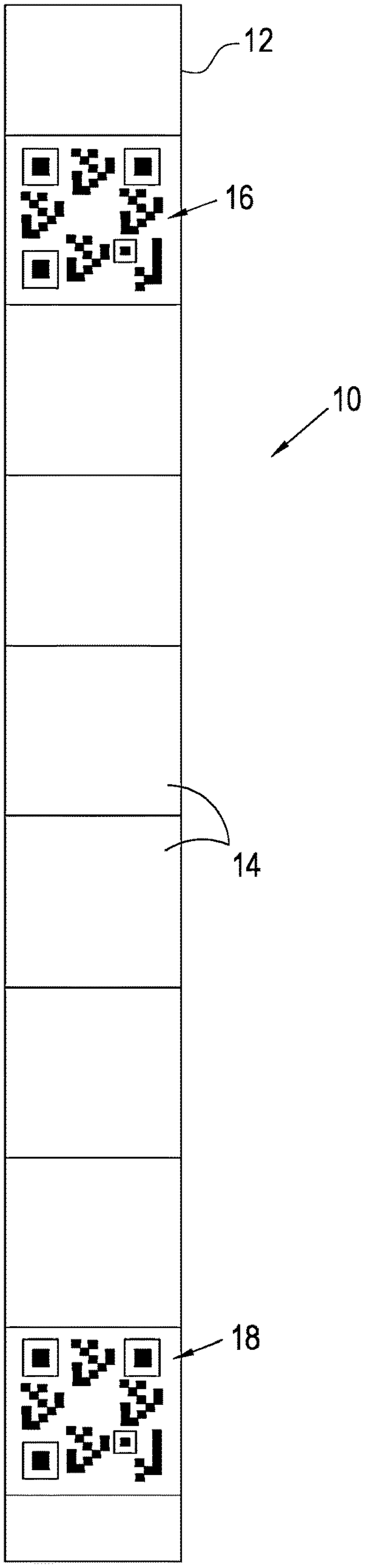
FIG. 3 shows another perspective view of an indicator in accordance with an example embodiment of the disclosure in a fully unfolded condition.

Referring to FIGS. 1 to 3 of the drawings, an indicator in accordance with an example embodiment of the disclosure is generally indicated by reference numeral 10. The indicator 10 is typically an indicator used to indicate that articles have been exposed to adequate sterilisation conditions. In particular, the indicator 10 is for use with medical articles which require sterilisation in autoclaves and is used to indicate adequate sterilisation thereof in a traceable manner as will be described further herein.

The indicator 10 has a planar strip-like body 12 which is segmented into a plurality of panels 14 which are folded in a concertina fashion as can be seen in FIGS. 1 and 2.

The indicator 10 is typically constructed from 80 gsm white medical grade paper and in some example embodiments has a substrate and an adhesive backed upper layer which may be peeled from the substrate in a label-fashion.

In some example embodiments, the panels 14 of the indicator 10 may be adhesively attached to adjacent panels but may be easily withdrawn from each other by pulling the end panels 14.1, 14.2 in the direction of arrows A and B, for example, as illustrated in FIG. 1. The concertina arrangement of the panels 14 limits the contact of the panels with metal surfaces as it does not lie flush with metal surfaces, for example, in an autoclave.

The indicator 10 advantageously comprises indicator machine-readable information 16 provided on the body, wherein the indicator machine-readable information is obscured from being read by a suitable reader device until the indicator, or a portion thereof comprising the indicator machine-readable information, is exposed to predetermined sterilisation condition/s. The predetermined sterilisation condition/s may be one, or more, of a predetermined temperature, moisture in the form of steam for a predetermined amount of time, and pressure encountered in an autoclave. To this end, the indicator machine-readable information 16 is printed on the body 12 and is revealed to be read by the suitable reader device in response to the predetermined sterilisation condition/s, which conditions may be present in or associated with an autoclave which sterilises articles. The ink which the information 16 is printed with may be conventional inks which may not be readable by a suitable optical reader device unless it is exposed to the predetermined sterilisation conditions, whereafter it is visible to an extent which enables reading by the suitable optical reader device. It will be noted that in one example embodiment, the indicator machine-readable information is invisible to the reader device and/or to the human eye but becomes visible after exposure to the predetermined sterilisation condition/s as described and/or as contemplated herein.

The indicator machine-readable information 16 may be in the form of a code which is readable by the suitable optical reader device. The code 16 may be a bar code, a Quick Response (QR) Code, or the like which is readable by the suitable reader device. To this end, the reader device may be a dedicated scanner device or a mobile computing device configured to read the code 16 as described herein. It will be appreciated that the by "reading the code 16", the suitable reader device is a capable of decoding/deciphering the information contained in or represented by the code 16.

The predetermined sterilisation conditions may be a temperature of approximately 134° C. and/or moisture as a result of exposure to saturated steam for a predetermined amount of time, for example, 3 minutes and/or a predetermined pressure associated with an autoclave. As mentioned, herein the indicator QR code 16 will only be exposed or revealed to an extent which is readable by the reader device in response to the indicator, or a portion thereof, being exposed to a predetermined temperature and/or pressure and/or moisture. In this way, the ability of the reader device to read the indicator machine-readable information may be indicative of the indicator, or part thereof, being exposed to a predetermined pressure and/or temperature and/or moisture, in other words desired sterilisation conditions.

The body 12 may further comprise article detail machine-readable information 18 which is also a QR code which may read by a suitable reader device to provide information indicative of a batch number and/or serial number associated with article/s associated with the indicator 10. The QR code 18 is typically plainly visible or readable by the reader device. which is configured to read the indicator machine-readable information may also be configured to read the article detail machine-readable information. In some example embodiments, the article detail machine-readable information comprises human readable information.

Figure 4:
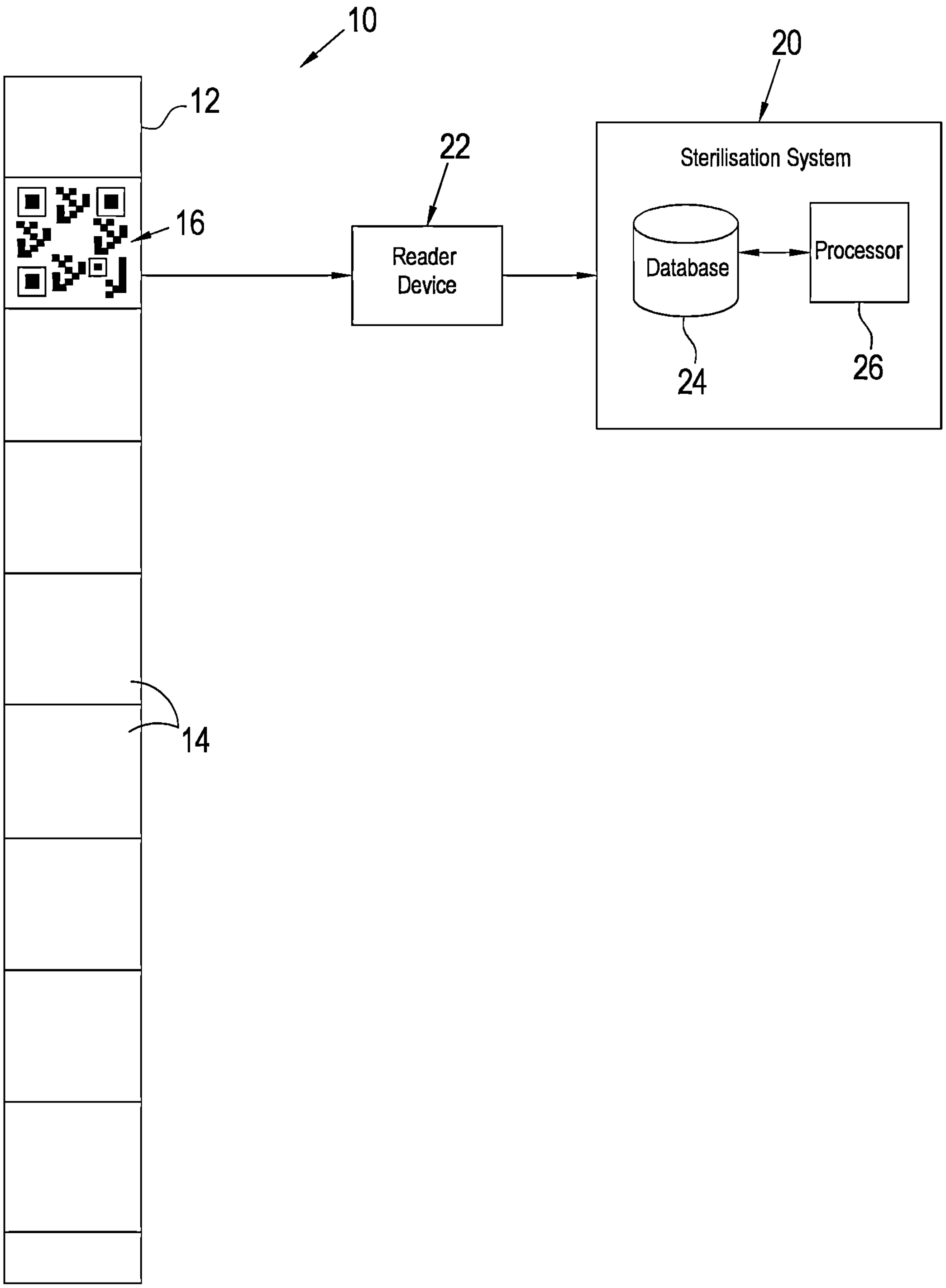
FIG. 4 shows a high-level schematic diagram of a system in accordance with an example embodiment of the disclosure for managing sterilisation of article/s.

Referring to FIG. 4 of the drawings, a system for managing sterilisation of articles in the form of medical equipment such as theatre sets is generally indicated by reference numeral 20. The system 20 is conveniently arranged to provide an auditable electronic trail for the sterilisation of medical equipment, for example, theatre sets, prostheses, or the like which are conventionally sterilised in an autoclave.

The system 20 is communicatively coupled to optical reader devices 22 which is capable of reading the QR codes 16, 18 of indicators 10 as described herein. Though only one reader device 22 is illustrated, it will be appreciated that the system 20 may be communicatively coupled to a plurality of reader devices 22, for example, via a suitable communication network (not shown). The communications network may comprise one or more different types of communication networks. In this regard, the communication networks may be one or more of the Internet, a local area network (LAN), a wide area network (WAN), a metropolitan area network (MAN), various types of telephone networks (e.g., Public Switch Telephone Networks (PSTN) with Digital Subscriber Line (DSL) technology) or mobile networks (e.g., Global System Mobile (GSM) communication, General Packet Radio Service (GPRS), Code Division Multiple Access (CDMA), and other suitable mobile telecommunication network technologies), or any combination thereof. It will be noted that communication within the network may achieved via suitable wireless or hard-wired communication technologies and/or standards (e.g., wireless fidelity (Wi-Fi®), 4G, long-term evolution (LTE™), WiMAX, 5G, and the like).

The reader devices 22 may form part of the system 20 and as alluded to above may be a dedicated scanner device to read the codes 16, 18 or a suitable mobile computing device having provided thereon software in the form of a software application downloaded and stored in a suitable memory of the mobile computing device which, when executed on said mobile computing device, causes the mobile computing device to read the codes 16, 18. To this end, the reader devices 22 may comprise one or more computer processors and a computer memory (including transitory computer memory and/or non-transitory computer memory), configured to perform various data processing and/or data storage operations, respectively.

It will be appreciated that the reader devices 22 with the software application running or operating thereon may be considered to be part of the system 20.

The reader devices 22 also include network communication interfaces (not shown) to connect to the system 20 via the communications network. Examples of the devices represented by the device 22 may be selected from a group comprising a personal computer, portable computer, smartphone, tablet, notepad, dedicated server computer devices, any type of communication device, and/or other suitable computing devices. It will be appreciated that in some example embodiments, the devices 22 may be connected to the communications network via an intranet, an Internet Service Provider (ISP) and the Internet, a cellular network, and/or other suitable network communication technology.

The system 20, or portions thereof, is typically embodied in one or more servers which are operatively communicatively connected to the communications network by suitable network interface/s. Though one server is illustrated, it will be appreciated that the system 20 may be incorporated in one or a plurality of networked servers spread out locally and/or geographically, for example, in a cloud-based computing like fashion.

Though not illustrated, it will be understood that the system 20 may include one or more of a back-end (e.g., a data server), a middleware (e.g., an application server), and a front-end (e.g., a client computing device having a graphical user interface (GUI) or a Web browser through which a user can interact with example implementations of the subject matter described herein). In a preferred example the example embodiment under discussion, the graphical user interface or Web browser may be rendered on the reader devices 22. In particular, the users may access the system 20 via the communications network by entering, on a web browser, a Uniform Resource Locator (URL) corresponding to a domain hosted by the system 10. Accordingly, a web page with the GUI is displayed on the reader device.

The system 20, particularly the one or more servers, may include a database 24 and one or more processor/s 26. The database 24 may be computer memories (including transitory computer memory and/or non-transitory computer memory). In particular, the database 24 may be in the form of computer-readable medium including system memory and including random access memory (RAM) devices, cache memories, non-volatile or back-up memories such as programmable or flash memories, read-only memories (ROM), etc. In addition, the database 24 may be considered to include memory storage physically located elsewhere in the system 20, e.g. any cache memory in the processor/s 26 as well as any storage capacity used as a virtual memory, e.g., as stored on a mass storage device.

The processor 26 may be one or more processors in the form of programmable processors executing one or more computer programs to perform actions by operating on input data and generating outputs. For brevity, a singular processor 26 will be referred to herein.

The processor 26, as well as any computing device referred to herein, may be any kind of electronic device with data processing capabilities including, by way of non-limiting example, a general processor, a graphics processing unit (GPU), a digital signal processor (DSP), a microcontroller, a field programmable gate array (FPGA), an application specific integrated circuit (ASIC), or any other electronic computing device comprising one or more processors of any kind, or any combination thereof. For brevity, steps described as being performed by the system 20 may be steps which are effectively performed by the processor 26 and vice versa unless otherwise indicated.

Though not illustrated, it will be appreciated that the system 20 may comprise one or more user input devices (e.g., a keyboard, a mouse, imaging device, scanner, microphone) and a one or more output devices (e.g., a Liquid Crystal Display (LCD) panel, a sound playback device (speaker), switches, valves, etc.).

It will be appreciated that the “computer programs” or “software applications” described herein, such as the software application executable by the reader devices 22, and/or the computer software executable by the processor 26 may be written in any form of programming language, including compiled or interpreted languages, declarative or procedural languages, and can be deployed in any form, including as a stand-alone program or as a module, component, subroutine, object, or other unit suitable for use in a computing environment. The computer program may, but need not, correspond to a file in a file system. The program can be stored in a portion of a file that holds other programs or data (e.g., one or more scripts stored in a mark-up language document), in a single file dedicated to the program in question, or in multiple coordinated files (e.g., files that store one or more modules, sub-programs, or portions of code). It will be understood that in the case of the processor 26, the computer program can be deployed to be executed by one processor 26 or by multiple processors 26, even those distributed across multiple locations, for example, in different servers and interconnected by the communication network.

The computer programs may be stored in the database 24 or in memory provided in the processor 26 as the case may be. Though not illustrated or discussed herein, it will be appreciated by those skilled in the field of disclosure that the system 20 may comprise a plurality of logic components, electronics, driver circuits, peripheral devices, etc. not described herein for brevity.

The processor 26 is configured to receive the QR codes 16, 18, or the information contained therein or represented thereby, via the reader devices 22 which are configured to read the codes 16, 18 as described herein. The reader devices 22 are typically able to read the codes 16, 18 by way of the software application operating thereon which is configured to instruct the suitable processor of the reader device 22 to operate an image capturing device, such as a camera associated with the device 22, to decrypt and read the codes 16, 18. To this end, the codes 16, 18 may be encrypted to prevent un-authorised reading thereof and thereby un-authorised access to a patient’s personal data.

When received, the codes read by the reader devices 22 may be in the form of numeric and/or alphanumeric and/or alphabet-based codes and/or other data associated therewith. Instead, or in addition, the codes read by the reader devices 22 may remain in a QR code format.

Once received, the processor 26 is configured to associate the indicator QR code 16 with the article QR code 18 and/or the specific article/s sanitised as described by the article QR code 18 in the database 24. In this way, the article sanitised is identified by the article QR code 18 and by the reading of the indicator QR code 16, which is made available for scanning by the reader device 22 by exposed to the sanitisation conditions, represents that the article has indeed been exposed to the desired and/or predetermined sanitisation conditions. This record is stored in the database as proof that that the article in question has indeed been sanitised or exposed to the sanitisation conditions required by medical facilities. In some example embodiments, the indicator QR code 16 and/or the article QR code 18 may be associated with a patient, particularly patient data associated therewith, in the database 24. The association may be done with a patient’s profile in the database 24 thus the database 24 may be associated with a healthcare facility.

As mentioned herein, the patient data may comprise any data to identify the patient including data selected from a group comprising the patient’s name, address, identity number, medical aid number, admission number, doctor’s details, medical procedure details, date/s of the procedure, and the like. In this way, an audit trail is generated and maintained in the database 26 which has a record of the patient, the articles or sets of articles used in their procedure and a record that the article or set of articles has been exposed to adequate sterilisation conditions.

It will be understood by those skilled in the art that this is very advantageous to healthcare workers and healthcare facilities as they will always be in a position to review a patient’s record and provide evidence in the form of a scanned indicator QR code 16 that any medical articles used in their procedure was duly sanitised by being exposed to the predetermined sanitisation conditions described herein.

In use, referring to FIGS. 1 to 4 of the drawings, when an article/s such as a theatre kit is required to be sanitised, for example, in a healthcare setting such as a hospital by way of an autoclave, the indicator 10 as described herein is provided with the theatre kit and is uniquely associated with the same via the article QR code 18. This may be done by a supplier of theatre sets.

It will be understood that to access with article QR code 18, the free end panels 14.1, 14.2 are pulled in the direction of arrows A and B and are opened in a concertina fashion. The article QR code is read by way of the reader device 22. In some example embodiments, the details of the article associated with the indicator is instead or in addition printed with the batch and expiry reference on the indicator 10. In this way, the specific theatre set is identifiable by the system 20.

Once read by the reader device 22, the article QR code, particularly the information contained therein or represented thereby is transmitted to the system 20 wherein the processor 26 stores the said information in the database 24 so that the specific theatre set is identifiable by the system 10. In this way, each indicator 10 is uniquely associated with a specific article, which in the example embodiment under discussion is a theatre set.

The specific theatre set with its associated indicator is then subjected to sterilisation procedures, typically in an autoclave. Once the predetermined sterilisation conditions have been met, the indicator QR code 16 which is not readable prior to the sterilisation, is available to be read by the reader device 22 which transmits the read data to the system 20 where the processor uniquely associates the information identifying the theatre set, i.e., as determined by the article QR code 18, with the indicator QR code 16, or information associated therewith, which indicates that the theatre set has been correctly sanitised by being exposed to the predetermined sterilisation conditions.

In some example embodiments, the indicator QR code 16 turns black or any other colour capable of being read by the reader devices 22 in response to the sterilisation conditions being met. Differently stated, the indicator machine-readable information 16 may change from an un-readable to a readable condition in response to exposure to the predetermined sterilisation condition/s, wherein in the un-readable condition, the indicator machine-readable information 16 is not readable by the suitable reader device 22, and in the readable condition, the indicator machine-readable information 16 is visible and/or visually presented and/or accessible and/or is revealed to be read by the suitable reader device 22. The change from the un-readable to the readable condition may be permanent. However, in some example embodiments, the change from the un-readable to the readable condition may be temporary. However, in the case wherein the visibility of the indicator machine-readable code 16 is temporary, it is long enough for the indicator machine-readable information 16 to be read by the suitable reader device 22. For example, a few minutes.

Though not illustrated, it will be appreciated that in some example embodiments, the indicator QR code 16 serves to identify the article as well as be readable by the reader device 22. In other words, in some example embodiments, the indicator 10 only has one QR code 16 which is readable upon exposure to the predetermined sterilisation conditions which also identifies the article/s.

In some example embodiments, the QR code may be attached adhesively to patient charge sheets so that the sterilised articles used for specific patients can be traced and associated in the database 24. As mentioned herein, a patients record stored in the database 24 may also indicate the specific theatre set used for their procedure as, for example, determined by the article QR code 18 as well as the indicator QR code 16, or information associated therewith, so that there is an auditable trail that the theatre set has been sterilised or exposed to predetermined sterilisation conditions.

It follows that if the indicator QR code 16 cannot be read by the reader device 22, it indicates that the articles in question have not been exposed to the predetermined sanitisation conditions and thus may not be adequately sanitised. It will be appreciated that the inability of the reader devices 22 to read or scan codes 16 will result in the system 20 not being able to input the associated articles or sets of articles, or data associated therewith, into the system 20 thus forcing healthcare personnel to re-sanitise or sanitise said articles or sets of articles. In this way, the safety of the patient in being treated with properly sanitised articles or sets of articles is enhanced.

Figure 5:
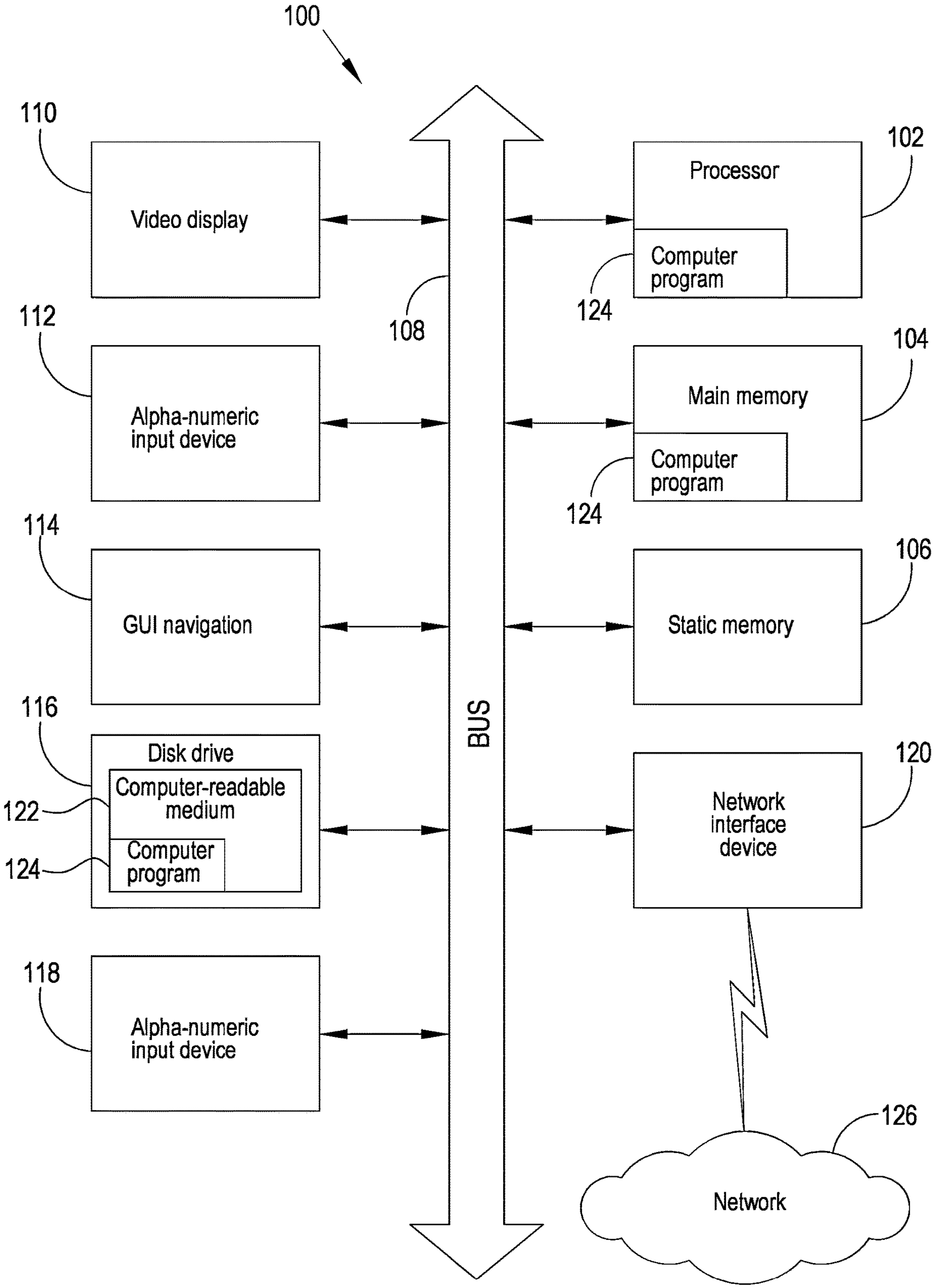
FIG. 5 shows a diagrammatic representation of a machine in the example form of a computer system in which a set of instructions for causing the machine to perform any one or more of the methodologies discussed herein, may be executed.

Referring now to FIG. 5 of the drawings which shows a diagrammatic representation of machine in the example of a computer system 100 within which a set of instructions, for causing the machine to perform any one or more of the methodologies discussed herein, may be executed. In other example embodiments, the machine operates as a standalone device or may be connected (e.g., networked) to other machines. In a networked example embodiment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated for convenience, the term "machine" shall also be taken to include any collection of machines, including virtual machines, that individually or jointly execute a set (or multiple sets) of instructions to perform any one or more of the methodologies discussed herein.

In any event, the example computer system 100 includes a processor 102 (e.g., a central processing unit (CPU), a graphics processing unit (GPU) or both), a main memory 104 and a static memory 106, which communicate with each other via a bus 108. The computer system 100 may further include a video display unit 110 (e.g., a liquid crystal display (LCD) or a cathode ray tube (CRT)). The computer system 100 also includes an alphanumeric input device 112 (e.g., a keyboard), a user interface (UI) navigation device 114 (e.g., a mouse, or touchpad), a disk drive unit 116, a signal generation device 118 (e.g., a speaker) and a network interface device 120.

The disk drive unit 16 includes a non-transitory machine-readable medium 122 storing one or more sets of instructions and data structures (e.g., software 124) embodying or utilised by any one or more of the methodologies or functions described herein. The software 124 may also reside, completely or at least partially, within the main memory 104 and/or within the processor 102 during execution thereof by the computer system 100, the main memory 104 and the processor 102 also constituting machine-readable media.

The software 124 may further be transmitted or received over a network 126 via the network interface device 120 utilising any one of a number of well-known transfer protocols (e.g., HTTP).

Although the machine-readable medium 122 is shown in an example embodiment to be a single medium, the term "machine-readable medium" may refer to a single medium or multiple medium (e.g., a centralized or distributed memory store, and/or associated caches and servers) that store the one or more sets of instructions. The term "machine-readable medium" may also be taken to include any medium that is capable of storing, encoding or carrying a set of instructions for execution by the machine and that cause the machine to perform any one or more of the methodologies of the present disclosure, or that is capable of storing, encoding or carrying data structures utilised by or associated with such a set of instructions. The term "machine-readable medium" may accordingly be taken to include, but not be limited to, solid-state memories, optical and magnetic media, and carrier wave signals.

The present disclosure as described herein provides a convenient way to manage the sanitisation of articles in an auditable manner in that the indicator QR codes 16 as described herein will not be able to be scanned into the system 20 unless it is exposed, together with the articles in question, to predetermined sanitisation conditions.

The invention claimed is:

1. An indicator comprising:

a body; and indicator machine-readable information provided on the body, wherein the indicator machine-readable information is configured to change from an unreadable condition to a readable condition in response to predetermined sterilisation conditions, said conditions comprising a predetermined temperature, predetermined moisture level, and predetermined pressure, wherein the body is segmented into a plurality of panels foldable in a concertina fashion.

2. The indicator as claimed in claim 1, wherein the predetermined temperature is approximately 134° C.

3. The indicator as claimed in claim 1, wherein the predetermined moisture level is as a result of exposure of the indicator to saturated steam for a predetermined amount of time.

4. The indicator as claimed in claim 3, wherein the predetermined amount of time is three minutes.

5. The indicator as claimed in claim 1, wherein the body comprises article detail machine-readable information which is indicative of a batch number and/or serial number associated with an article.

6. The indicator as claimed in claim 1, wherein the machine-readable information is in the form of a Quick Response Code (QR code) or a barcode.

7. The indicator as claimed in claim 1, wherein the indicator machine-readable information, or data associated therewith, is encrypted and/or is only readable by an authorised reader device.

8. The indicator as claimed in claim 1, wherein the indicator machine-readable information is associated with a patient, or patient data associated with the patient.

* * * * *